(12) United States Patent
Matsuura

(10) Patent No.: US 8,403,835 B2
(45) Date of Patent: Mar. 26, 2013

(54) ENDOSCOPE SYSTEM AND DRIVE CONTROL METHOD THEREOF

(75) Inventor: Hideo Matsuura, Saitama (JP)

(73) Assignee: Fujifilm Corporation, Tokyo (JP)

( * ) Notice: Subject to any disclaimer, the term of this patent is extended or adjusted under 35 U.S.C. 154(b) by 561 days.

(21) Appl. No.: 12/556,481

(22) Filed: Sep. 9, 2009

(65) Prior Publication Data

US 2010/0063352 A1 Mar. 11, 2010

(30) Foreign Application Priority Data

Sep. 10, 2008 (JP) ................................. 2008-231891

(51) Int. Cl.
*A61B 1/06* (2006.01)
(52) U.S. Cl. ...................................................... 600/177
(58) Field of Classification Search .................. 600/109, 600/160, 177; 396/17; 348/68, 70
See application file for complete search history.

(56) References Cited

U.S. PATENT DOCUMENTS

| 5,667,474 | A | 9/1997 | Nishimura |
| 6,570,615 | B1 | 5/2003 | Decker et al. |
| 7,745,771 | B2 | 6/2010 | Troxell et al. |
| 2003/0176768 | A1* | 9/2003 | Gono et al. ................. 600/109 |
| 2006/0149133 | A1* | 7/2006 | Sugimoto et al. ........... 600/160 |
| 2007/0014553 | A1 | 1/2007 | Endo |
| 2008/0018733 | A1 | 1/2008 | Hasegawa |

FOREIGN PATENT DOCUMENTS

| JP | 1-280440 A | 11/1989 |
| JP | 6-062438 A | 3/1994 |
| JP | 6-276529 | 9/1994 |
| JP | 6-327627 A | 11/1994 |
| JP | 7-246184 | 9/1995 |
| JP | 2002/095635 | 4/2002 |
| JP | 2004-321244 A | 11/2004 |
| JP | 2007-244681 A | 9/2007 |

OTHER PUBLICATIONS

U.S. Appl. No. 12/385,219, filed Apr. 1, 2009 (Hiroshi Yamaguchi, et al.).
Japanese Office Action dated Sep. 27, 2012 and English translation thereof.
United States Office Action dated Apr. 24, 2012, in U.S. Appl. No. 12/556,496.
United States Notice of Allowance dated Mar. 16, 2012, in U.S. Appl. No. 12/561,050.
United States Office Action dated Nov. 15, 2012, in U.S. Appl. No. 12/385,219.

* cited by examiner

*Primary Examiner* — Clayton E LaBalle
*Assistant Examiner* — Noam Reisner
(74) *Attorney, Agent, or Firm* — McGinn IP Law Group, PLLC

(57) ABSTRACT

A movement detection circuit analyzes image data from a DSP, and detects an amount of movement of an object relative to a solid-state image sensor. A CPU compares a movement detection value with a threshold value. When the movement detection value is the threshold value or less, a normal light source and a special light source are alternately turned on and off at intervals of charge accumulation time of the solid-state image sensor. Normal light moving images and special light moving images are simultaneously displayed on a screen. When the movement detection value exceeds the threshold value, write of the special light moving images is inhibited. A display control circuit displays on the screen one of the normal light moving images, a special light still image, and tiled windows for simultaneously showing the normal light moving images and special light still image.

12 Claims, 6 Drawing Sheets

ENDOSCOPE SYSTEM AND DRIVE CONTROL METHOD THEREOF

BACKGROUND OF THE INVENTION

1. Field of the Invention

The present invention relates to an endoscope system that selectively applies normal light such as white light and special light such as infrared light to an internal body part, and a drive control method thereof.

2. Description Related to the Prior Art

A medical examination using an electronic endoscope is widely available in recent years. The electronic endoscope has a solid-state image sensor such as CCD at a distal portion of an insert section to be introduced into a human body cavity. The electronic endoscope is connected to a processor device and a light source device through a cord and a connector.

The processor device applies signal processing to a pickup signal outputted from the solid-state image sensor to produce an endoscope image. The endoscope image is displayed on a monitor connected to the processor device. The light source device has a white light source such as a xenon lamp. The light source device supplies the electronic endoscope with the white light to illuminate an internal body part.

In the field of medical diagnosis using the electronic endoscope, a method called Narrow Band Imaging (hereinafter abbreviated as NBI) sits in the limelight. In the NBI, light with a narrow wavelength band (hereinafter called special light) is applied to the internal body part, instead of the white light (hereinafter called normal light), which has broad spectral characteristic in a visible light range, and reflection of the special light forms an image. An image taken under illumination of the normal light will be called as a normal light image, and an image under illumination of the special light will be called a special light image. The NBI allows easy obtainment of an image that emphasizes a blood vessel beneath the mucous membrane and an image that emphasizes components of an organ such as a stomach wall and intestine cortex tissue, and hence facilitates finding out a lesion.

Japanese Patent Laid-Open Publication No. 2002-095635 or U.S. Pat. No. 5,667,474 (corresponding to Japanese Patent Laid-Open Publication No. 07-246184) proposes an endoscope system adopting the NBI. In such an endoscope system, a filter that integrally includes a normal light filtering section and a special light filtering section is disposed in an optical path of light from a light source. The filter is mechanically moved by a motor or the like in response to switching operation of an operator (doctor), so as to obtain both of the normal and special light images.

An endoscope system according to Japanese Patent Laid-Open Publication No. 2002-095635 (corresponding to U.S. Patent Application Publication No. 2003/0176768) is provided with a rotational filter that selectively outputs the normal light and special light. Switching from the normal light to the special light reduces light intensity. Accordingly, it is described in paragraph [0043] to extend exposure time in special light observation. Extending the exposure time, however, increases fluctuation in the image. Thus, the endoscope system is provided with a movement detection circuit for detecting movement of an object. When it is judged that there is no movement during freeze operation, an image stored on an image memory is updated. When there is movement, the image is not updated. In sixth and seventh embodiments described in paragraphs [0089] to [0106], a xenon lamp is used as a normal light source, and a super-high pressure mercury lamp is used as a special light source.

U.S. Pat. No. 5,667,474 discloses a field sequential image pickup apparatus that is provided with a filter and a movement detection circuit as with above. In this apparatus, when it is judged that an object has moved during normal light observation, freeze operation is inhibited. When it is judged that there is movement during special light observation, an adder suspends adding operation (noise reduction operation). When it is judged that there is no movement, the adder resumes the noise reduction operation.

Japanese Patent Laid-Open Publication No. 06-276529 also discloses an image pickup device having a movement detection circuit. In this device, the degree of contour emphasis varies in accordance with the degree of movement of an object. In other words, the slower the object moves, the more a contour signal is emphasized.

In the NBI, it is demanded to display the normal light image and the special light image simultaneously on a single screen for the purpose of making diagnosis with comparing both images in detail. However, there is a relatively large gap between the timing of taking the two images. If an object moves during an interval between the two images, simultaneity (equality) is not maintained. Accordingly, the doctor cannot carry out precise comparison and make correct diagnosis.

In Japanese Patent Laid-Open Publication No. 2002-095635 and U.S. Pat. No. 5,667,474, the filter is mechanically moved, and the normal light image and special light image are separately displayed. The normal and special light images are selectively switchable, but cannot be displayed together. In addition, neither of the systems intends to maintain the simultaneity of the images. Relative movement of the object is detected, but detection result is used only for judging whether or not to update image data during the freeze operation, or whether or not to carry out the freeze operation and noise reduction operation. None of the foregoing documents considers simultaneity in displaying the normal and special light images on the single screen.

SUMMARY OF THE INVENTION

An object of the present invention is to provide an endoscope system that can achieve simultaneity of a normal light image and a special light image in displaying the both images on a single screen at the same time, and a drive control method thereof.

An endoscope system includes a solid-state image sensor, a light source device, a movement detection circuit, and a display control circuit. The solid-state image sensor converts image light of an object inside a body cavity into a pickup signal. The light source device alternately applies normal light and special light to the object at intervals of charge accumulation time of the solid-state image sensor. The special light has different spectral characteristic from the normal light. The movement detection circuit detects an amount of movement of the object relative to the solid-state image sensor. The display control circuit simultaneously displays both of normal light moving images taken under illumination of the normal light and special light moving images taken under illumination of the special light on a single screen. If a movement detection value detected by the movement detection circuit has exceeded a threshold value, the display control circuit prohibits write of the special moving images.

The light source device has a normal light source for emitting the normal light having a broad band and a special light source for emitting the special light having a narrow band. The display control circuit displays on the screen one of the normal light moving images taken under illumination of the normal light, the special light moving images taken under illumination of the special light, tiled windows for displaying the normal light moving images and the special light moving images at the same time in a tiled manner, and superimposed moving images for superimposing the normal light moving images and the special light moving images.

When the movement detection value of the movement detection circuit has exceeded the threshold value, the display control circuit displays on the screen one of the normal light moving images taken under illumination of the normal light, a normal light still image taken under illumination of the normal light, a special light still image taken under illumination of the special light, and tiled windows for showing the normal light moving images and the special light still image at the same time.

A method for controlling drive of an endoscope system includes the steps of alternately applying normal light and special light to an object inside a body cavity at intervals of charge accumulation time of a solid-state image sensor, simultaneously displaying normal light moving images taken under illumination of the normal light and special light moving images taken under illumination of the special light on a single screen, detecting an amount of movement of the object relative to the solid-state image sensor, and inhibiting write of the special light moving images if the amount of movement exceeds a threshold value.

According to the present invention, when the object moves relatively fast, write of the special light moving images is inhibited. Accordingly, the simultaneity between the normal light moving images and the special light moving images (special light still image) is maintained in simultaneously displaying the both images on a single monitor. Therefore, it is possible to compare the both images in detail for diagnosis.

BRIEF DESCRIPTION OF THE DRAWINGS

For more complete understanding of the present invention, and the advantage thereof, reference is now made to the following descriptions taken in conjunction with the accompanying drawings, in which.

DESCRIPTION OF THE PREFERRED EMBODIMENTS

Figure 1:
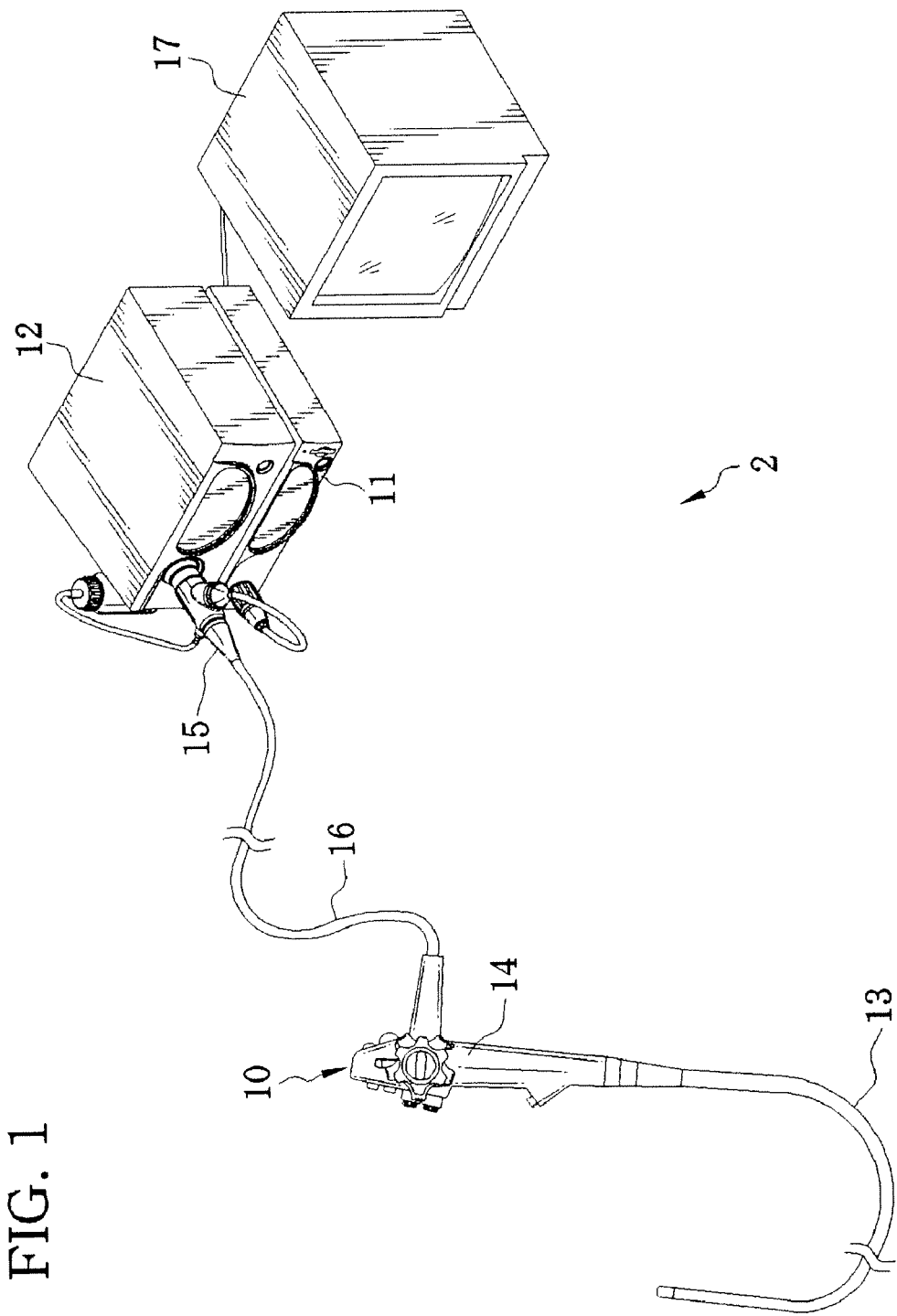
FIG. 1 is an external view of an endoscope system.

In FIG. 1, an endoscope system 2 is constituted of an electronic endoscope 10, a processor device 11, and a light source device 12. The electronic endoscope 10 has a flexible insert section 13 to be introduced into a human body cavity, a handling section 14 coupled to a base end of the insert section 13, a connector 15 connected to the processor device 11 and the light source device 12, and a universal cord 16 for connecting between the handling section 14 and the connector 15.

Figure 2:
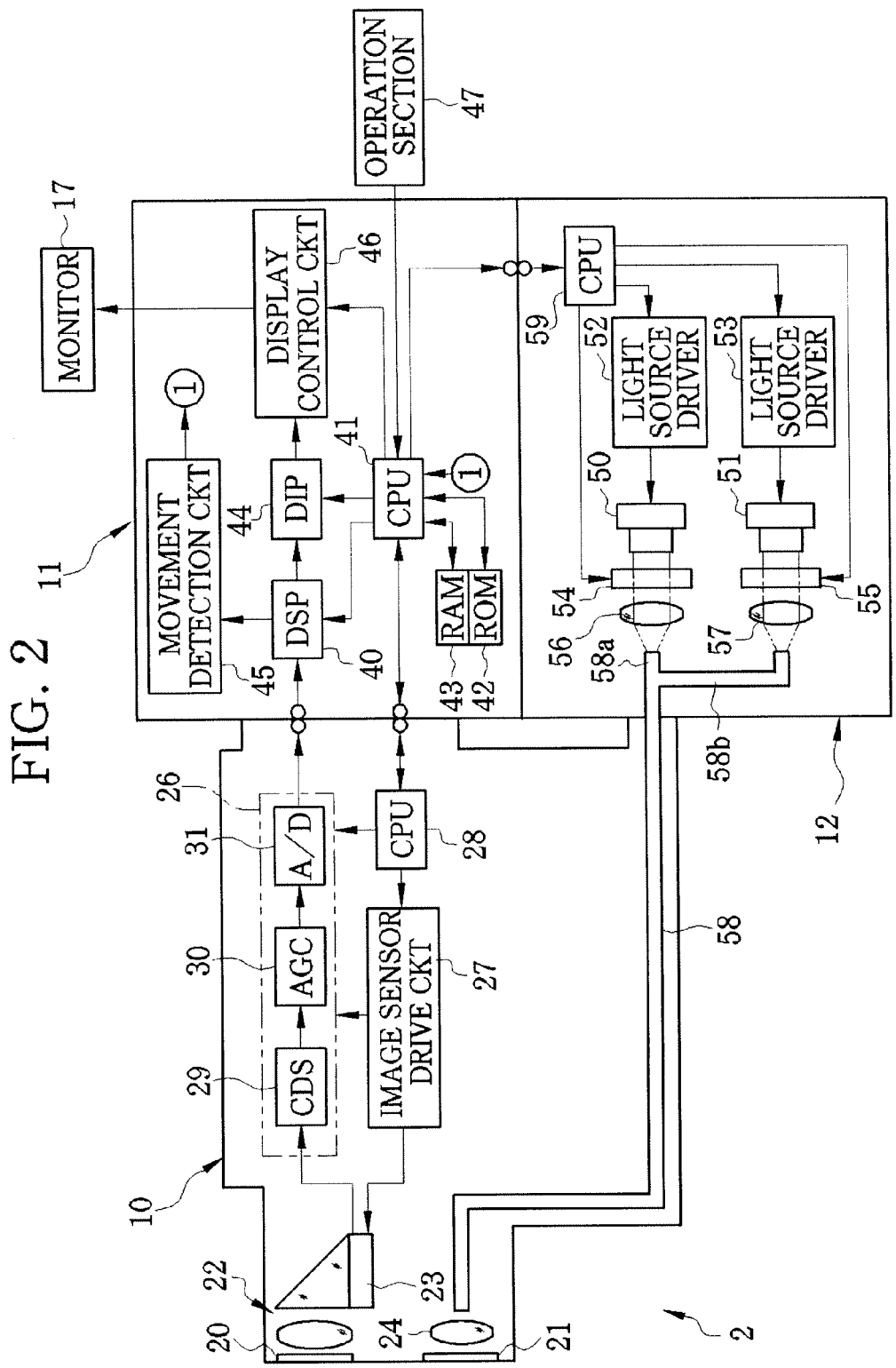
FIG. 2 is a block diagram showing the structure of the endoscope system.

Referring to FIG. 2, an image capture window 20, a lighting window 21 and the like are provided at a distal end face of the insert section 13. Behind the image capture window 20, a solid-state image sensor 23 is disposed through an objective optical system 22, and captures an image of an internal body part. Light from the light source device 12 is lead through a light guide 58, which extends through the universal cord 16 and the insert section 13, and is incident on the internal body part through a lighting lens 24 and the lighting window 21.

On the handling section 14, there are provided an angle knob for bending a distal end portion of the insert section 13 side to side and up and down, an airing/watering button for ejecting air or water from the distal end portion of the insert section 13, a release button for capturing a still image of the internal body part, and the like.

A medical instrument insertion port to which a medical instrument such as a radio knife is inserted is provided on the handling section 14 on the side of a distal end. The medical instrument insertion port leads to a medical instrument outlet, which is provided at the distal end face of the insert section 13, through a channel in the insert section 13.

The processor device 11 is electrically connected to the light source device 12, and controls the entire operation of the endoscope system 2. The processor device 11 feeds electric power to the electronic endoscope 10 through a transmission cable extending through the universal cord 16 and the insert section 13, and controls actuation of the solid-state image sensor 23. The processor device 11 receives a pickup signal from the solid-state image sensor 23 through the transmission cable. The processor device 11 applies various processes to the pickup signal to produce image data. The produced image data is displayed as an endoscopic image on a screen of a monitor 17, which is connected to the processor device 11 with a wire.

In the electronic endoscope 10, as shown in FIG. 2, the distal end portion of the insert section 13 contains the objective optical system 22, the solid-state image sensor 23, and the lighting lens 24. The handling section 14 contains an analog front end processor (AFE) 26, an image sensor drive circuit 27, and a CPU 28.

The solid-state image sensor 23 is, for example, an interline transfer CCD, a CMOS image sensor, or the like. The objective optical system 22 is composed of a lens group and a prism. The solid-state image sensor 23 is so disposed that image light of the internal body part that has passed through the image capture window 20 and the objective optical system 22 is incident upon its image capture surface. The image capture surface of the solid-state image sensor 23 is equipped with a color filter (for example, Bayer array primary-color filter) consisting of a plurality of color segments.

The AFE 26 includes a correlated double sampling circuit (CDS) 29, an automatic gain controller (AGC) 30, and an A/D converter (A/D) 31. The CDS 29 applies correlated double sampling to the pickup signal from the solid-state image sensor 23 in order to remove reset noise and amplification noise produced in the solid-state image sensor 23. The AGC 30 amplifies the pickup signal without noise by gain (amplification factor) designated by the processor device 11. The A/D 31 converts the amplified pickup signal into a predetermined bit number of digital pickup signal. The digital pickup signal from the A/D 31 is inputted to the processor device 11 through the universal cord 16 and the connector 15, and is temporarily stored on a working memory (not illustrated) of a digital signal processor (DSP) 40.

The image sensor drive circuit 27 generates drive pulses (vertical and horizontal scanning pulses, reset pulses, and the like) for the solid-state image sensor 23 and a synchronization pulse for the AFE 26. The solid-state image sensor 23 captures an image based on the drive pulses from the image sensor drive circuit 27, and outputs the pickup signal. Each of the components 29 to 31 of the AFE 26 operates based on the synchronization pulse from the image sensor drive circuit 27.

After the electronic endoscope 10 is connected to the processor device 11, the CPU 28 drives the image sensor drive circuit 27 in response to an operation start command from the CPU 41, and adjusts the gain of the AGC 30.

The CPU 41 controls the entire operation of the processor device 11. The CPU 41 is connected to every part through not-illustrated data buses, address buses, and control lines. A ROM 42 stores various programs (an OS, application programs, and the like) for controlling the operation of the processor device 11 and data (graphic data and the like). The CPU 41 reads the required programs and data from the ROM 42. Then, the CPU 41 loads the programs and data into a RAM 43 being a working memory, and successively processes the read programs. The CPU 41 retrieves data that varies from examination to examination or from patient to patient such as text data describing an examination date, a patient's name and a doctor's name from a database through a network such as a LAN (local area network), and stores the data on the RAM 43.

The DSP 40 reads the pickup signal produced by the AFE 26 from the working memory. The DSP 40 applies various signal processing such as color separation, color interpolation, gain correction, white balance adjustment and gamma correction to the pickup signal to generate image data. The image data generated by the DSP 40 is inputted to a working memory (not illustrated) of a digital image processor (DIP) 44 and a movement detection circuit 45.

The DIP 44 carries out various image processing based on the control of the CPU 41. The DIP 44 reads the image data processed by the DSP 40 from the working memory. The DIP 44 applies the various image processing such as electronic scaling, color enhancement, edge enhancement and the like to the image data. The image data processed by the DIP 44 is inputted to a display control circuit 46.

The display control circuit 46 has a VRAM for storing the image data processed by the DIP 44. The CPU 41 transfers the graphic data from the ROM 42 and the RAM 43 to the display control circuit 46. The graphic data includes a mask data that covers an invalid pixel region and shows only a valid pixel region, the text data including the examination date, the patient's name and the doctor's name, a graphical user interface (GUI) and the like. The display control circuit 46 subjects the image data from the DIP 44 to various types of display control processing such as superimposition of the mask data, text data and GUI, and drawing of the image data on the monitor 17.

The display control circuit 46 reads the image data from the VRAM, and converts the image data into a video signal (component video signal, composite video signal or the like) compliant to a display format of the monitor 17. Accordingly, moving images are displayed on the screen of the monitor 17.

The movement detection circuit 45 has a frame memory that stores successive two frames of image data from the DSP 40. The movement detection circuit 45 compares the two frames of image data stored on the frame memory, and detects a movement vector of an object by an ordinarily known method. For example, pattern matching is used, in which, retrieving a pixel corresponding to an equal point of the object from each of the two frames of images, spatial distance and direction between the pixels are detected as the movement vector. The movement detection circuit 45 outputs the magnitude of the detected movement vector (an amount of movement of the observed portion relative to the solid-state image sensor 23) to the CPU 41.

An operation section 47 includes an operation panel provided in a case of the processor device 11 and commonly-known input devices such as a mouse and keyboard. The CPU 41 operates individual part in response to an operation signal from the operation section 47.

The processor device 11 is provided with an image compression circuit for compressing the image data by a predetermined compression format (for example, JPEG format), a medium I/F for writing the compressed image data into a removable medium such as a CF card, a magneto-optical disk (MO) and a CD-R, and a network I/F for controlling transfer of various data over the network such as the LAN, in addition to the above. The image compression circuit, the medium I/F, the network I/F and the like are connected to the CPU 41 thorough data buses.

The light source device 12 has two light sources, that is, a normal light source (broad-bandwidth light source) 50 and a special light source (narrow-bandwidth light source) 51. The normal light source 50 is, for example, a xenon lamp or a white LED, and emits light in a broad bandwidth from red to blue (hereinafter called normal light). The special light source 51 is, for example, a blue LED or LD (laser diode), and emits light having a wavelength in a specific narrow bandwidth (hereinafter called special light). The special light source 51 emits light in an arrow bandwidth around 450, 500, 550, 600 or 780 nm separately or by combining some.

The light sources 50 and 51 are driven by light source drivers 52 and 53, respectively. An aperture stop 54 is disposed on a light emitting side of the light source 50 to increase or decrease an amount of light incident on a condenser lens 56. In a like manner, an aperture stop 55 is disposed on a light emitting side of the light source 51 to increase or decrease an amount of light incident on a condense lens 57. The condenser lenses 56 and 57 condense light that has passed through the aperture stops 54 and 55, respectively, and lead the light to entries of the light guide 58.

The CPU 59 communicates with the CPU 41 of the processor device 11 to control the operation of the light source drivers 52 and 53 and the aperture stops 54 and 55. The light led to a light emitting end of the light guide 58 is diffused by the lighting lens 24, and is applied to the internal body part through the lighting window 21.

The light guide 58 consists of, for example, a bundle of silica optical fibers wound with a tape. Two light guides 58a and 58b, which are disposed on the light emitting sides of the light sources 50 and 51, respectively, are merged into the single light guide 58 in the light source device 12 by commonly known optical fiber multiplexing technology or Y-coupling technology.

By operating the operation section 47, the endoscope system 2 is switchable between a normal light mode (broad-bandwidth light mode) for emitting the normal light and a special light mode (narrow-bandwidth light mode) for emitting the special light.

In the normal light mode, the CPU 41 controls the light source drivers 52 and 53 via the CPU 59 so as to turn on the normal light source 50 and turn off the special light source 51. Thus, only the normal light is applied to the object. In the special light mode, on the other hand, the CPU 41 alternately turns on and off the normal light source 50 and the special light source 51 at intervals of charge accumulation time of the solid-state image sensor 23. Accordingly, the normal light and special light are alternately applied to the object at intervals of the charge accumulation time of the solid-state image sensor 23.

Figure 3:
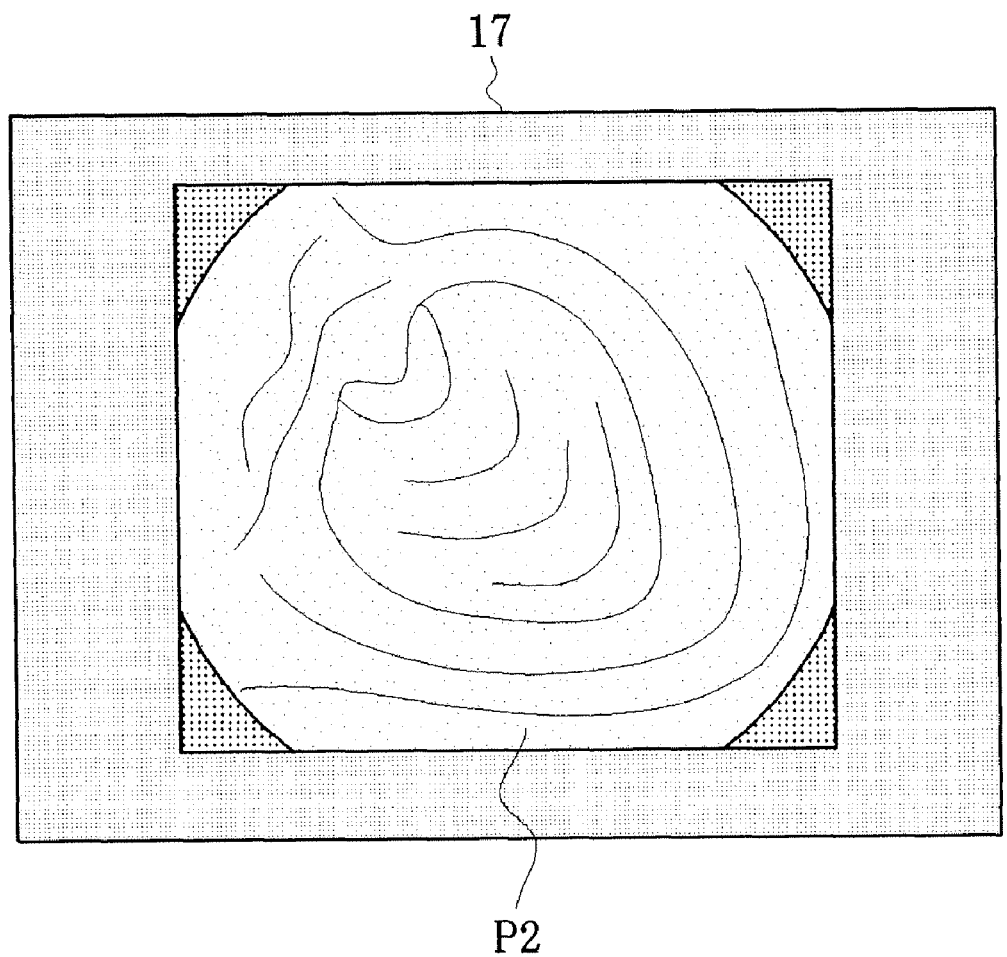
FIG. 3 is an explanatory view showing an example of displaying special light moving images.
Figure 4:
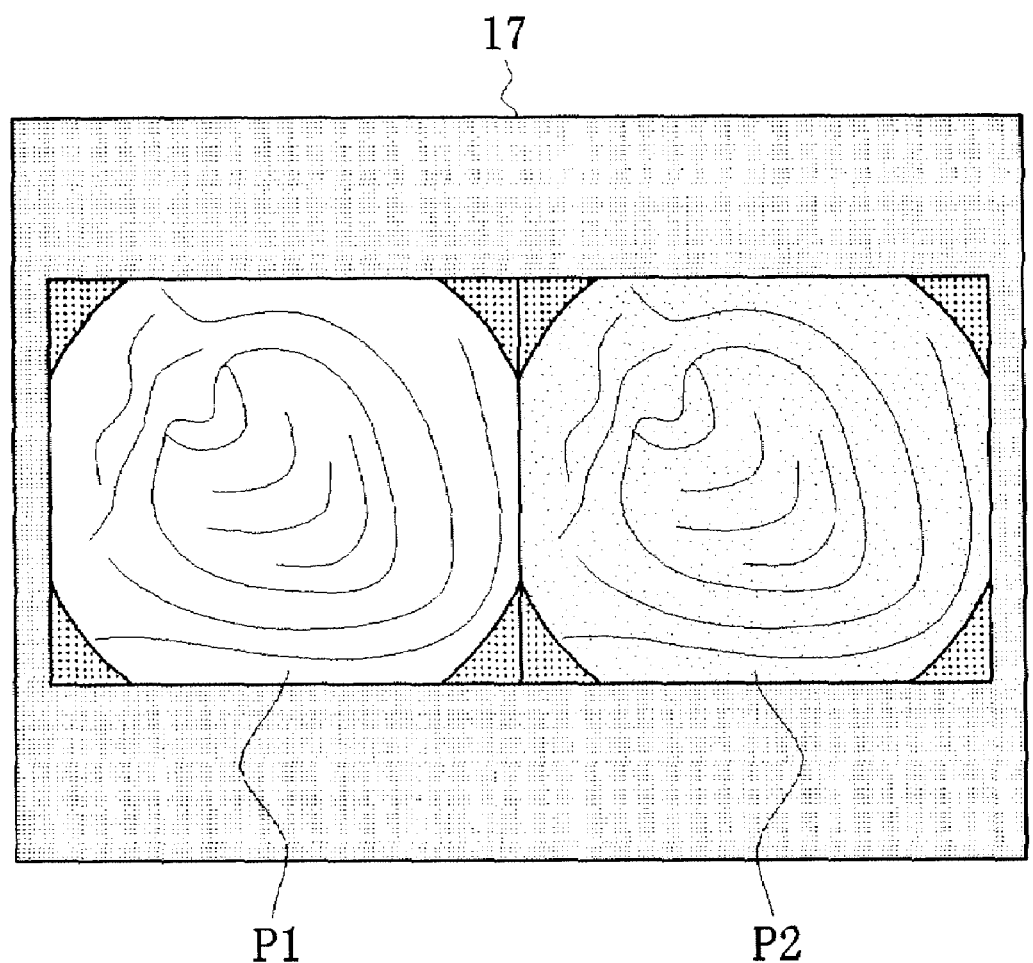
FIG. 4 is an explanatory view showing an example of displaying normal light moving images and the special light moving images in a single screen.
Figure 5:
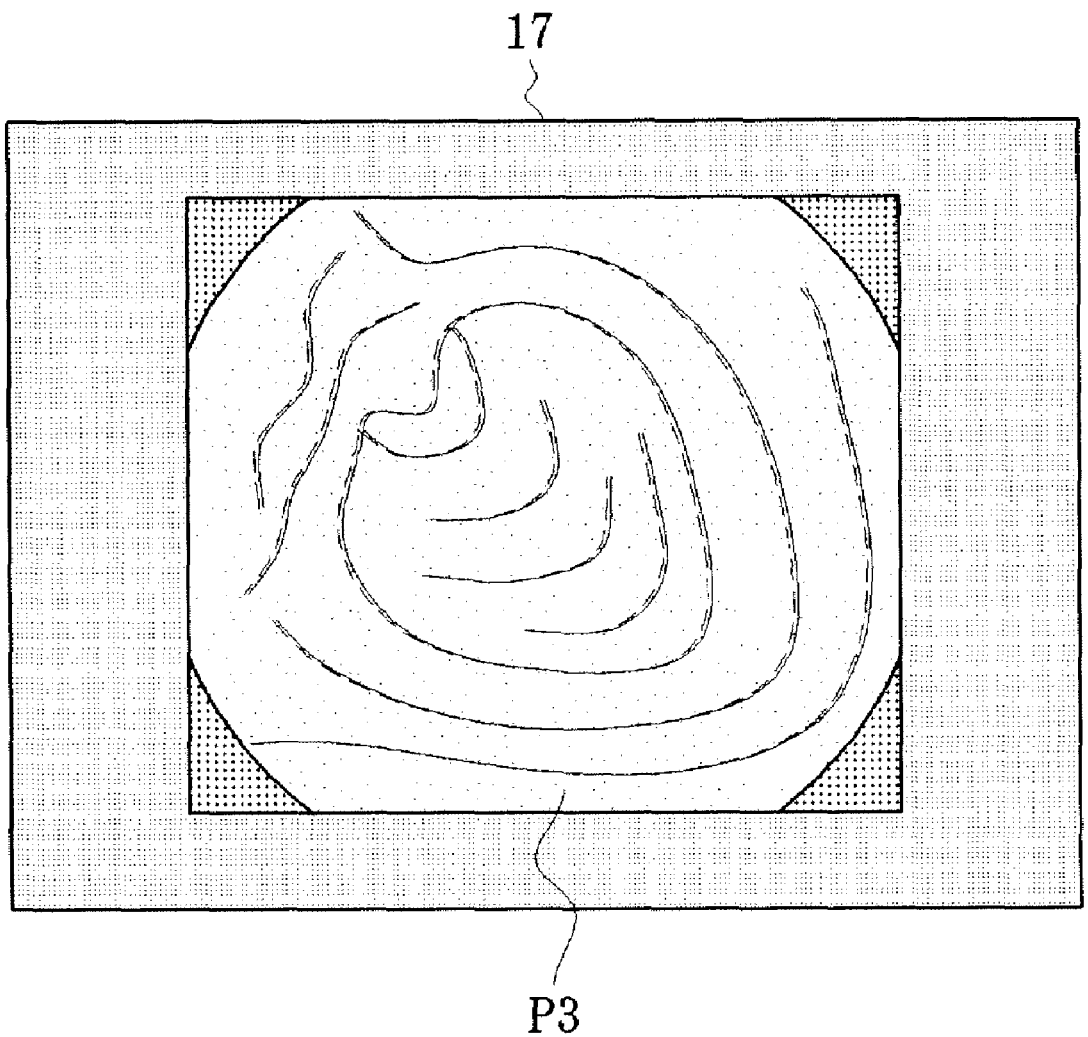
FIG. 5 is an explanatory view showing an example of displaying superimposed moving images.

Referring to FIGS. 3 to 5, P2 is moving images that are generated from the pickup signal taken under illumination of the special light (hereinafter called special light moving images) P1 is moving images that are generated from the pickup signal taken under illumination of the normal light (hereinafter called normal light moving images). P3 is moving images into which the normal light moving images and the special light moving images are superimposed or overlaid (hereinafter called superimposed moving images). In the special light mode, the display control circuit 46 displays one of the special light moving images P2 (see FIG. 3), windows that display the normal light moving images P1 and the special light moving images P2 in a tiled manner (see FIG. 4), and the superimposed moving images P3 (see FIG. 5) on the monitor 17. Operation of the operation section 47 switches the display. In the normal light mode, the normal light moving images P1 are displayed on the monitor 17, as a matter of course. It is also possible to display the normal light moving images P1 in the special light mode. In the special light mode, a frame rate of the moving images is reduced by one-half of that in the normal light mode.

When the endoscope system 2 is in the special light mode and a detection value of the movement detection circuit 45 is a threshold value or less, in other words, when the movement of the object relative to the solid-state image sensor 23 is slow, the normal light source 50 and the special light source 51 are alternately turned on and off at intervals of the charge accumulation time of the solid-state image sensor 23. The display control circuit 46 displays endoscopic images in a display style chosen by the operation section 47.

On the other hand, when the detection value of the movement detection circuit 45 exceeds the threshold value, in other words, when the movement of the object relative to the solid-state image sensor 23 is fast, the CPU 41 prohibits write of the special light moving images P2 on the VRAM, while keeping alternately turning on and off the normal light source 50 and the special light source 51. The CPU 41 commands the display control circuit 46 to automatically switch display on the monitor 17. Accordingly, the normal light moving images P1 or a still image (special light still image) P2' that is taken under illumination of the special light is displayed on the monitor 17. In some instances, the CPU 41 also prohibits write of the normal light moving images P1, and displays a still image (normal light still image) P1' that is taken under illumination of the normal light.

When the relatively large movement of the object is detected while the special light moving images P2 are displayed on the monitor 17 as shown in FIG. 3, the display control circuit 46 switches the display to the normal light moving images P1 or the special light still image P2'. When the relatively large movement is detected while the superimposed moving images P3 are displayed on the monitor 17 as shown in FIG. 5, superimposition of the special light moving images P2 is suspended, so that only the normal light moving images P1 are displayed.

When the relatively large movement is detected while the normal light moving images P1 and the special light moving images P2 are displayed in a tiled manner, as shown in FIG. 4, the display control circuit 46 switches the display into full display of the normal light moving images P1, or keeps tiled windows and displays the normal light moving images P1 on the left window and switches the special light moving images P2 to the special light still image P2' on the right window. In the latter case, the normal light still image P1' may be displayed instead of the normal light moving images P1. The display may be switched from a style of FIG. 5 into the tiled windows shown in FIG. 4. Note that the term of the tiled windows is used to express a window area according to an image tiling mode well-known in the art and containing at least two adjacent sub window regions.

Next, the operation of the endoscope system 2 will be described. In observing inside the patient's body cavity by the electronic endoscope 10, a doctor connects the electronic endoscope 10 to the processor device 11 and the light source device 12, and turns on the processor device 11 and the light source device 12. Then, the doctor inputs patient's data and the like from the operation section 47, and starts examination.

The insert section 13 is introduced into the patient's body cavity. The doctor monitors the endoscopic images, which are captured by the solid-state image sensor 23 under light from the light source device 12, of the internal body part on the screen of the monitor 17.

The pickup signal from the solid-state image sensor 23 is subjected to various processing by the AFE 26, and then inputted to the DSP 40 of the processor device 11. The DSP 40 applies various signal processing to the pickup signal, and generates the image data. The image data is inputted to the DIP 44 and the movement detection circuit 45.

The DIP 44 applies image processing to the image data from the DSP 40 under the control of the CPU 41. The processed image data is stored on the VRAM of the display control circuit 46. The display control circuit 46 carries out various display control processing with the use of graphic data from the CPU 41. Thus, the image data is displayed on the monitor 17 as the endoscopic image.

When the normal light mode is chosen by the operation section 47, the CPU 41 turns on the normal light source 50 and turns off the special light source 51, so that only the normal light is applied to the object. The normal light moving images P1 taken under illumination of the normal light are displayed on the monitor 17.

Figure 6:
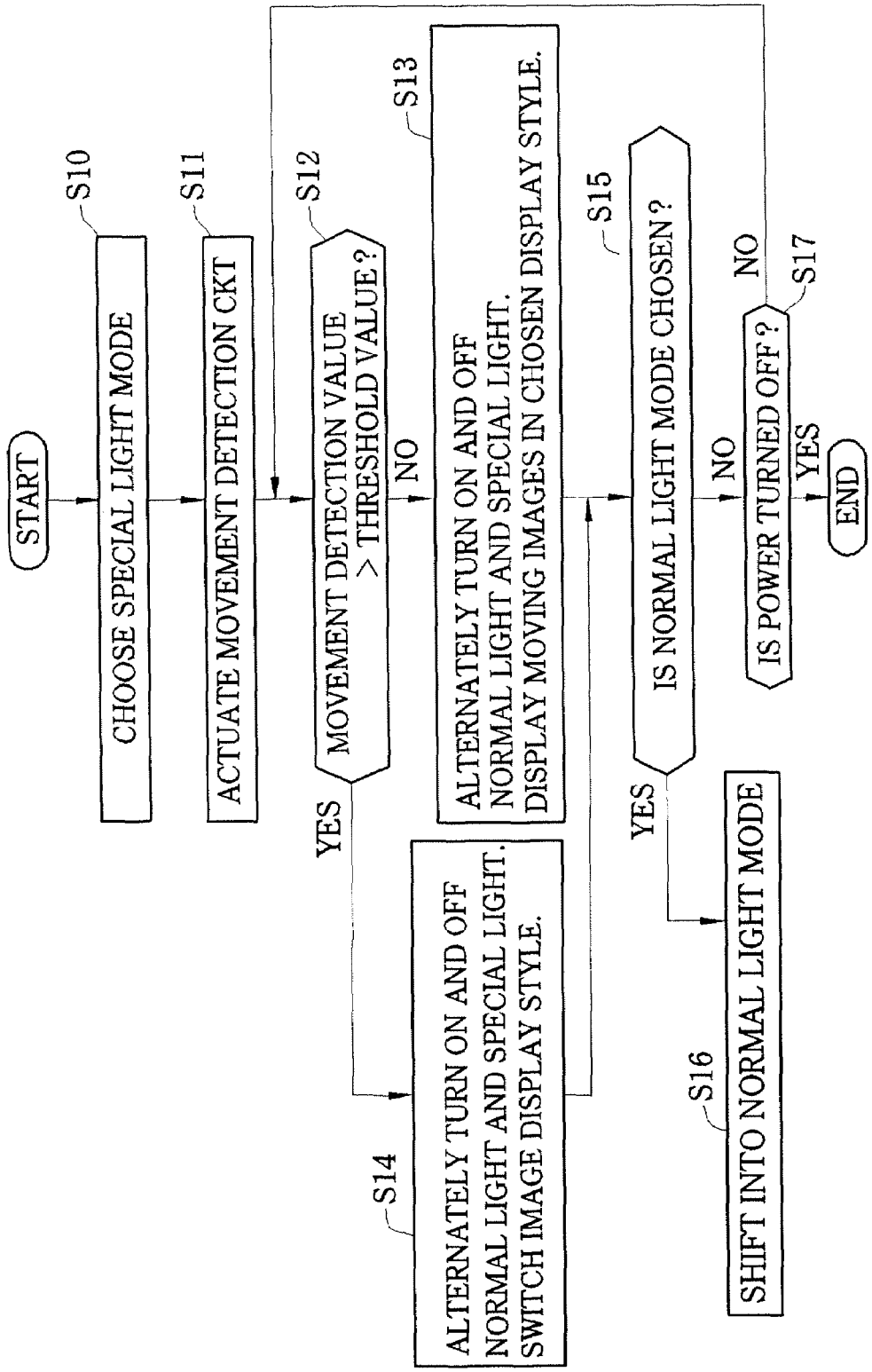
FIG. 6 is a flowchart showing a processing procedure in a special light mode.

When the special light mode is chosen by the operation section 47, as shown in step (S) 10 of FIG. 6, the movement detection circuit 45 is actuated (S11). The movement detection circuit 45 detects the movement detection value, and inputs the value to the CPU 41. The CPU 41 compares the movement detection value with the threshold value.

When the movement detection value is the threshold value or less (NO in S12), the operation proceeds to S13. The CPU 41 alternately turns on and off the normal light source 50 and special light source 51 at intervals of the charge accumulation time of the solid-state image sensor 23. The normal light and special light are alternately applied to the object at intervals of the charge accumulation time of the solid-state image sensor 23. The moving images are displayed on the monitor 17 in a display style chosen from FIGS. 3 to 5 by the operation section 47.

When the movement detection value exceeds the threshold value (YES in S12), on the other hand, the operation proceeds to S14. The CPU 41 alternately turns on and off the normal light source 50 and special light source 51 at intervals of the charge accumulation time of the solid-state image sensor 23, as with S13. The normal light and special light are alternately applied to the object, but write of the special light moving images P2 on the VRAM is prohibited. The display control circuit 46 automatically switches display on the monitor 17 into one of the normal light moving images P1, the special light still image P2', and the tiled windows showing the normal light moving images P1 and the special light still image P2'. Instead of the normal light moving images P1, the normal light still image P1' may be displayed. A procedure from S12 to S14 is repeated until the normal light mode is chosen (YES in S15) for a shift into the normal light mode (S16) or electric power is turned off (YES in S17).

As described above, the movement detection circuit 45 detects an amount of movement of the object relative to the solid-state image sensor 23. Since write of the special light moving images P2 is prohibited when the movement detection value exceeds the threshold value, it is possible to maintain simultaneity of the normal light moving images P1 and the special light moving images P2 in displaying the both images on the screen of the monitor 17 at the same time.

When the movement detection value exceeds the threshold value, the movement of the object is relatively fast. Thus, the object moves between capture of a single frame of the normal light moving images P1 and capture of a corresponding frame of the special light moving images P2. The movement of the object causes deterioration in image quality such as out-of-color registration and fluctuation in edges in the superimposed moving images P3, into which the normal light moving images P1 and the special light moving images P2 are superimposed, but the present invention can prevent such a problem. This is because when the movement detection value exceeds the threshold value, write of the special light moving images P2 on the VRAM is prohibited and creation of the superimposed moving images P3 is suspended. When the tiled windows showing the normal light moving images P1 and the special light moving images P2 have been displayed, the display on the monitor 17 is automatically switched, for the purpose of preventing misdiagnosis of the doctor.

When the doctor introduces the insert section 13 of the electronic endoscope 10 into the patient's body cavity toward a region of interest, it is conceivable that the solid-state image sensor 23 moves fast. In other words, the movement of the object relative to the solid-state image sensor 23 is fast. The movement detection value of the movement detection circuit 45 exceeds the threshold value. One or some of the normal light moving images P1, the special light still image P2' and the normal light still image P1' is/are displayed on the monitor 17, but the display does not affect observation and diagnosis, because the imaging or diagnosis is not essential in the course of travel of the insert section 13.

When the distal end portion of the insert section 13 has reached the region of interest such as a lesion and the doctor is observing there in detail, the solid-state image sensor 23 does not move so much. Namely, the movement of the object relative to the solid-state image sensor 23 is slow. In this case, the normal light and special light are alternately applied to the object at intervals of the charge accumulation time of the solid-state image sensor 23. One of the special light moving images P2, the tiled windows showing the normal light moving images P1 and the special light moving images P2, and the superimposed moving images P3 is displayed. The doctor can conveniently choose the display style suited for diagnosis.

When the large movement is detected, the special light moving images P2 in the tiled windows are switched into the special light still image P2', and the superimposed moving images P3 are switched into the normal light moving images P1. Thus, the monitor 17 always displays images without out-of-color registration or fluctuation in edges. Accordingly, the appearance of the endoscopic images displayed on the monitor 17 does not change so much, and the doctor and patient do not visually feel strangeness, anxiety or confusion.

The normal light source 50 and special light source 51 are easy to control because of being driven in constant states, irrespective of a comparison result between the movement detection value and the threshold value.

Alternate emission of the normal light and the special light at intervals of the charge accumulation time of the solid-state image sensor 23 brings about alternate output of frames of the normal light moving images P1 and special light moving images P2. The frame memory of the movement detection circuit 45 stores the latest two frames of the normal light moving images P1, that is, a current frame of the normal light moving images P1 and a frame captured two frames earlier than the current frame among those. A frame of the special light moving images P2 that is captured between the stored two frames of the normal light moving images P1 is abandoned. The movement detection circuit 45 compares the two frames of the normal light moving images P1 to detect the movement vector, but may detect the movement from two frames of the special light moving images P2 instead.

When the movement detection value frequently crosses the threshold value in a short time, the display on the monitor 17 may be switched whiningly. Therefore, it is preferable that the sampling rate of the movement detection circuit 45 be set at an appropriate value. Otherwise, it is preferable to give hysteresis characteristic to the comparison between the movement detection value and the threshold value, and switch the display when the movement detection value has exceeded threshold value $\pm\alpha$.

There is the movement detection circuit 45 in the foregoing embodiment, but the DSP 40 or DIP 44 may have such function instead. Otherwise, a three-axis accelerometer or angular accelerometer (gyro sensor) may be provided at the distal end portion of the insert section 13 of the electronic endoscope 10 in order to detect the movement of the distal end portion relative to the object.

In the foregoing embodiment, prohibiting write on the VRAM of the display control circuit 46 stops capture of the special light moving images P2. However, the pickup signal of the special light moving images P2 outputted from the solid-state image sensor 23 may be abandoned, or the DSP 40 or DIP 44 stops generating the special light moving images P2 instead.

In the foregoing embodiment, the two light sources 50 and 51 emit the normal light and special light, respectively. Instead of the two light sources 50 and 51, for example, is available an LED or LD that can change the wavelength of emission light in response to a drive current. In this case, substituting a single light source for the two light sources 50 and 51 allows reduction in part costs and space.

A disk-shaped filter that integrally has a normal light filtering section and a special light filtering section may be used instead. The filter is disposed in an optical path of light from a light source, and is rotated in one direction so that the two filtering sections alternately cross the optical path at intervals of the charge accumulation time of the solid-state image sensor 23. Composing the filter as an adapter that is detachably attached to the distal end portion of the insert section 13 of the electronic endoscope 10 has such advantage as applying the present invention to an ordinary endoscope system having a white light source such as a xenon lamp only by changing its software.

The foregoing embodiment uses one light guide 58, but may be provided with two light guides for each of the light sources 50 and 51.

As another style of displaying the normal light moving images P1 and the special light moving images P2 on the single screen at the same time, the so-called Picture in Picture (PinP) may be used by which a picture is displayed on a full screen at the same time as another picture is displayed in an inset window.

The threshold value may be changeable by operation on the operation section 47. When the special light mode is chosen, the doctor may choose whether or not to switch the display style in response to detection result of the movement detection circuit 45. This allows the doctor to use the endoscope system 2 as intended.

When display of the special light moving images P2 is chosen in the special light mode, the normal light source 50 may be turned off and only the special light source 51 may be turned on, instead of alternately turning on and off both of the light sources 50 and 51. In this case, the special light moving images P2 can be captured at every frame.

The present invention may be applied to an ultrasound endoscope, instead of the electronic endoscope 10. The processor device and the light source device may be formed as an integral unit, instead of separated ones.

Although the present invention has been fully described by the way of the preferred embodiment thereof with reference to the accompanying drawings, various changes and modifications will be apparent to those having skill in this field. Therefore, unless otherwise these changes and modifications depart from the scope of the present invention, they should be construed as included therein.

What is claimed is:

1. An endoscope system, comprising:
   a solid-state image sensor for converting image light of an object inside a body cavity into a pickup signal;
   a light source device for alternately applying a normal light and a special light to said object at intervals of charge accumulation time of said solid-state image sensor, said special light having a different spectral characteristic from said normal light;
   a movement detection circuit for detecting an amount of a movement of said object relative to said solid-state image sensor; and
   a display control circuit for simultaneously displaying of normal light moving images taken under an illumination of said normal light and special light moving images taken under an illumination of said special light on a single screen,
   wherein, when a movement detection value detected by said movement detection circuit exceeds a threshold value, said display control circuit prohibits a write of said special moving images without prohibiting a write of said normal light moving images.

2. The endoscope system according to claim 1, wherein said light source device comprises a normal light source for emitting said normal light having a broad band and a special light source for emitting said special light having a narrow band.

3. The endoscope system according to claim 1, wherein said display control circuit displays on said screen one of said normal light moving images taken under the illumination of said normal light, said special light moving images taken under the illumination of said special light, tiled windows for displaying said normal light moving images and said special light moving images at a same time in a tiled manner, and superimposed moving images for superimposing said normal light moving images and said special light moving images.

4. The endoscope system according to claim 1, wherein, when said movement detection value of said movement detection circuit exceeds said threshold value, said display control circuit displays on said screen one of said normal light moving images taken under the illumination of said normal light, a normal light still image taken under the illumination of said normal light, a special light still image taken under the illumination of said special light, and tiled windows for showing said normal light moving images and said special light still image at a same time.

5. A method for controlling drive of an endoscope system, said method comprising:
   alternately applying a normal light and a special light to an object inside a body cavity at intervals of charge accumulation time of a solid-state image sensor;
   simultaneously displaying normal light moving images taken under an illumination of said normal light and special light moving images taken under an illumination of said special light on a single screen;
   detecting an amount of a movement of said object relative to said solid-state image sensor; and
   inhibiting a write of said special light moving images when said amount of said movement exceeds a threshold value without prohibiting a write of said normal light moving images.

6. The endoscope system according to claim 1, wherein, when said movement detection value exceeds said threshold value, said light source device continues to apply the normal light and the special light to said object alternately.

7. The endoscope system according to claim 1, wherein, when said movement detection value exceeds said threshold value, said display control circuit continues to display said normal light moving images.

8. The endoscope system according to claim 7, wherein, when said movement detection value exceeds said threshold value, said display control circuit stops said simultaneously displaying of said normal light moving images and said special light moving images.

9. The method of claim 5, wherein, when said amount of said movement exceeds said threshold value, said displaying on said screen comprises a display of one of said normal light moving images taken under the illumination of said normal light, a normal light still image taken under the illumination of said normal light, a special light still image taken under the illumination of said special light, and tiled windows for showing said normal light moving images and said special light still image at the same time.

10. The method of claim 5, wherein, when said amount of said movement exceeds said threshold value, the normal light and the special light continue to be alternately applied to said object.

11. The method of claim 5, wherein, when said amount of said movement exceeds said threshold value, said normal light moving images continue to be displayed on the single screen.

12. The method of claim 11, wherein, when said amount of said movement exceeds said threshold value, said simultaneously displaying of said normal light moving images and said special light moving images is stopped.

* * * * *